(12) United States Patent
Tekulve et al.

(10) Patent No.: US 8,831,707 B2
(45) Date of Patent: Sep. 9, 2014

(54) TIP DEFLECTING PUNCTURE NEEDLE

(75) Inventors: Kurt J. Tekulve, Ellettsville, IN (US);
Elizabeth A. Theobald, Bloomington, IN (US); Carrie Lynn Fercik, Ellettsville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 168 days.

(21) Appl. No.: 13/297,447

(22) Filed: Nov. 16, 2011

(65) Prior Publication Data
US 2013/0123620 A1 May 16, 2013

(51) Int. Cl.
*A61M 25/00* (2006.01)
(52) U.S. Cl.
USPC ............ 600/435; 604/528; 604/264; 604/523
(58) Field of Classification Search
None
See application file for complete search history.

(56) References Cited

U.S. PATENT DOCUMENTS

| | | | | |
|---|---|---|---|---|
| 5,221,269 A * | 6/1993 | Miller et al. | ................... | 604/528 |
| 5,508,802 A * | 4/1996 | Boehme et al. | ............... | 356/73.1 |
| 5,601,582 A * | 2/1997 | Shelton et al. | ................ | 606/170 |
| 6,508,802 B1 | 1/2003 | Rosengart et al. | ............ | 604/523 |
| 6,572,593 B1 | 6/2003 | Daum | ........................... | 604/264 |
| 6,758,830 B1 * | 7/2004 | Schaer et al. | ............... | 604/95.04 |
| 6,805,676 B2 * | 10/2004 | Klint | .............................. | 600/585 |
| 7,033,345 B2 * | 4/2006 | Lee et al. | ....................... | 604/528 |
| 7,402,151 B2 * | 7/2008 | Rosenman et al. | ......... | 604/95.05 |
| 7,559,924 B2 * | 7/2009 | Webler | ........................... | 604/506 |
| 7,815,608 B2 * | 10/2010 | Schafersman et al. | ... | 604/164.01 |
| 7,842,041 B2 * | 11/2010 | Liu et al. | .......................... | 606/94 |
| 7,850,644 B2 * | 12/2010 | Gonzalez et al. | .......... | 604/96.01 |
| 7,935,108 B2 * | 5/2011 | Baxter et al. | ..................... | 606/15 |
| 8,029,470 B2 * | 10/2011 | Whiting et al. | ............ | 604/164.01 |
| 8,226,709 B2 * | 7/2012 | Groothuis et al. | ............ | 623/2.11 |
| 8,267,932 B2 * | 9/2012 | Baxter et al. | ...................... | 606/41 |
| 2003/0083613 A1 * | 5/2003 | Schaer | ........................ | 604/95.04 |
| 2004/0181188 A1 * | 9/2004 | Schaer et al. | .............. | 604/95.04 |
| 2005/0222557 A1 * | 10/2005 | Baxter et al. | ..................... | 606/16 |
| 2005/0222558 A1 * | 10/2005 | Baxter et al. | ..................... | 606/16 |
| 2005/0234436 A1 * | 10/2005 | Baxter et al. | ..................... | 606/14 |
| 2005/0234437 A1 * | 10/2005 | Baxter et al. | ..................... | 606/15 |
| 2006/0074398 A1 * | 4/2006 | Whiting et al. | ............... | 604/510 |

(Continued)

OTHER PUBLICATIONS

Feldman, Ted et al., Transseptal puncture, in Problem Oriented Approaches in Interventional Cardiology, Apr. 2007, p. 203-216 and 218, Informa Healthcare, UK, available at http://www.northshore.org/UploadedFiles/cardiology/forphysicians/InterventionalRadiology/6_2007_IntCardioArticle1.PDF.

(Continued)

*Primary Examiner* — Nicholas Evoy
(74) *Attorney, Agent, or Firm* — Brinks Gilson & Lione

(57) ABSTRACT

A method of puncturing an interatrial septum between a right atrium and a left atrium may include introducing a distal end of a catheter endoluminally into the right atrium. The method also may include introducing a distal end of a cannula into the right atrium. The cannula may include a proximal first segment and a distal second segment. The distal second segment may be deflectable away from a linear configuration relative to the proximal first segment. A needle tip may be provided at a distal end of the distal second segment. At least a portion of the cannula may be received within a lumen of the catheter. The method also may include deflecting the distal second segment in the right atrium to a deflected configuration by actuating a mechanism at a proximal end of the cannula to align the needle tip with a target point on the interatrial septum.

19 Claims, 8 Drawing Sheets

(56) References Cited

U.S. PATENT DOCUMENTS

| | | | |
|---|---|---|---|
| 2007/0123804 A1* | 5/2007 | Ayala et al. .................... | 600/585 |
| 2009/0105654 A1* | 4/2009 | Kurth et al. .............. | 604/170.03 |
| 2009/0259304 A1* | 10/2009 | O'Beirne et al. ............ | 623/2.11 |
| 2009/0275934 A1* | 11/2009 | Baxter et al. ..................... | 606/15 |
| 2010/0185172 A1* | 7/2010 | Fabro ........................... | 604/500 |
| 2010/0198056 A1* | 8/2010 | Fabro et al. ................... | 600/424 |
| 2010/0280604 A1* | 11/2010 | Zipory et al. ................ | 623/2.11 |
| 2011/0066233 A1* | 3/2011 | Thornton et al. ............ | 623/2.11 |
| 2011/0245822 A1* | 10/2011 | Baxter et al. .................... | 606/21 |
| 2011/0245828 A1* | 10/2011 | Baxter et al. .................... | 606/41 |
| 2012/0010490 A1* | 1/2012 | Kauphusman et al. ........ | 600/373 |
| 2012/0130217 A1* | 5/2012 | Kauphusman et al. ........ | 600/373 |
| 2012/0130218 A1* | 5/2012 | Kauphusman et al. ........ | 600/373 |
| 2013/0012923 A1* | 1/2013 | Baxter et al. .................. | 604/523 |
| 2013/0013057 A1* | 1/2013 | Salahieh et al. ............. | 623/2.11 |

OTHER PUBLICATIONS

Disposable Reuter Tip Deflecting Wire Guides, posted on or before Jun. 2011, p. 1, Cook Medical, available at http://www.cookmedical.com/di/dataSheet.do?id=4434.

* cited by examiner

TIP DEFLECTING PUNCTURE NEEDLE

TECHNICAL FIELD

This disclosure relates generally to medical devices and methods of use. More particularly, it relates to surgical instruments for accurately puncturing the interatrial septum between the right and left atria of the heart.

BACKGROUND

The transseptal puncture technique may be used to gain access to the left atrium. Such access may be used to measure the left atrial pressure. As the number of valve replacement, valvoplasty, ablation, and other procedures has increased, the transseptal puncture technique has become increasingly popular as a method for accessing the left atrium.

The transseptal puncture technique generally involves introducing a catheter or sheath into the right femoral vein and guiding the catheter into the superior vena cava. A needle then is advanced within the catheter. The catheter and needle assembly is retracted into the right atrium. The right atrial pressure may be measured to confirm the position of the needle within the right atrium. The interatrial septum is punctured by advancing the needle tip through a portion of the interatrial septum. For example, the needle tip may be advanced through the fossa ovalis. Once the tip of the needle is inside the left atrium, the left atrial pressure may be measured.

When the transseptal puncture technique is used as a part of any one of a number of different procedures, the location of the transseptal puncture may be critical. In many cases, it may be difficult to align the tip of the needle with the fossa ovalis to puncture the interatrial septum at a precise location. This difficulty may be caused by variations in either or both of the diameter and the membrane consistency of the fossa ovalis. A needle having a preset curve may be provided to aid in puncturing the interatrial septum at the desired location. However, different needles having different degrees of curvature may be required depending on the anatomy of an individual patient. For example, one patient's anatomy may require a needle having a greater degree of curvature than another patient's anatomy. Additionally, a curved needle may lose its curvature (e.g., the needle may be at least partially straightened) upon advancing the needle through the catheter. In either case, a physician may be required to remove the needle, readjust the curvature or select another needle having a different curvature, and reintroduce the needle to puncture the interatrial septum at the desired location. A delivery catheter having a curved or otherwise steerable tip may be used to guide a needle received within the catheter in the desired direction. However, such delivery catheters often have bulky actuating mechanisms that may be difficult to operate.

Thus, it may be desirable to provide a transseptal puncture needle capable of conforming to various anatomies for placement at a precise location on the interatrial septum.

SUMMARY

The present embodiments provide a surgical instrument for accurately puncturing the interatrial septum between the right and left atria of the heart.

In one example, a method of puncturing an interatrial septum between a right atrium and a left atrium may include introducing a distal end of a catheter endoluminally into the right atrium. The catheter may include an elongate tubular member. The method also may include introducing a distal end of a cannula into the right atrium. The cannula may include an elongate tubular member having a proximal first segment and a distal second segment. The distal second segment of the cannula may be deflectable away from a linear configuration relative to the proximal first segment of the cannula. A needle tip may be provided at a distal end of the distal second segment of the cannula. The needle tip may have a lumen in fluid communication with a lumen of the cannula and a distal end having a distal end opening. At least a portion of the cannula may be received within a lumen of the catheter. The method also may include deflecting the distal second segment of the cannula in the right atrium to a deflected configuration by actuating a mechanism at a proximal end of the cannula. The distal second segment may be deflected to align the needle tip with a target point on the interatrial septum.

In another example, a medical instrument may include an elongate tubular cannula having a proximal end, a distal end, and a lumen extending between the proximal and distal ends of the cannula. The cannula may include a first segment and a second segment. The first segment of the cannula may be substantially longitudinally incompressible. The second segment of the cannula may be positioned distal of the first segment. At least a portion of the second segment of the cannula may be longitudinally compressible. A needle tip may extend from a distal end of the second segment of the cannula. The needle tip may have a proximal end, a sharpened distal end, and a needle lumen extending between the proximal and distal ends of the needle tip. The needle lumen may be in communication with the lumen of the cannula. An actuating member may extend longitudinally within the lumen of the cannula. The actuating member may have a proximal end and a distal end. The distal end of the actuating member may be attached to the second segment of the cannula. The second segment of the cannula may be movable between a neutral configuration in which a longitudinal axis of the second segment is substantially linear and a deflected configuration in which the longitudinal axis of the second segment is curved. Longitudinal movement of the actuating member relative to the cannula may cause movement of the second segment of the cannula between the neutral configuration and the deflected configuration.

In yet another example, a system for puncturing a body tissue of a patient may include an elongate tubular catheter having a proximal end, a tapered distal end, and a lumen extending between the proximal and distal ends of the catheter. The system also may include an elongate tubular cannula received within the lumen of the catheter. The cannula may have a proximal end, a distal end, and a lumen extending between the proximal and distal ends of the cannula. A first segment of the cannula may be substantially longitudinally incompressible. A second segment of the cannula may be positioned distal of the first segment. At least a portion of the second segment of the cannula may be longitudinally compressible. The system also may include a needle tip extending from the distal end of the second segment of the cannula. The needle tip may have a proximal end, a sharpened distal end, and a needle lumen extending between the proximal and distal ends of the needle tip. The needle lumen may be in communication with the lumen of the cannula. The system also may include an actuating member extending longitudinally within the lumen of the cannula. The actuating member may have a proximal end and a distal end. The distal end of the actuating member may be attached to the second segment of the cannula. The second segment of the cannula may be movable between a neutral configuration in which a longitudinal axis of the second segment is substantially linear and a deflected configuration in which the longitudinal axis of the second segment is curved. Longitudinal movement of the actuating member relative to the cannula may cause movement of the second segment of the cannula between the neutral configuration and the deflected configuration.

Other systems, methods, features, and advantages of the invention will be, or will become, apparent to one with skill in the art upon examination of the following figures and detailed description. It is intended that all such additional systems, methods, features, and advantages be within the scope of the invention, and be encompassed by the following claims.

BRIEF DESCRIPTIONS OF THE DRAWINGS

DETAILED DESCRIPTION OF THE DRAWINGS AND THE PRESENTLY PREFERRED EMBODIMENTS

Figure 1:
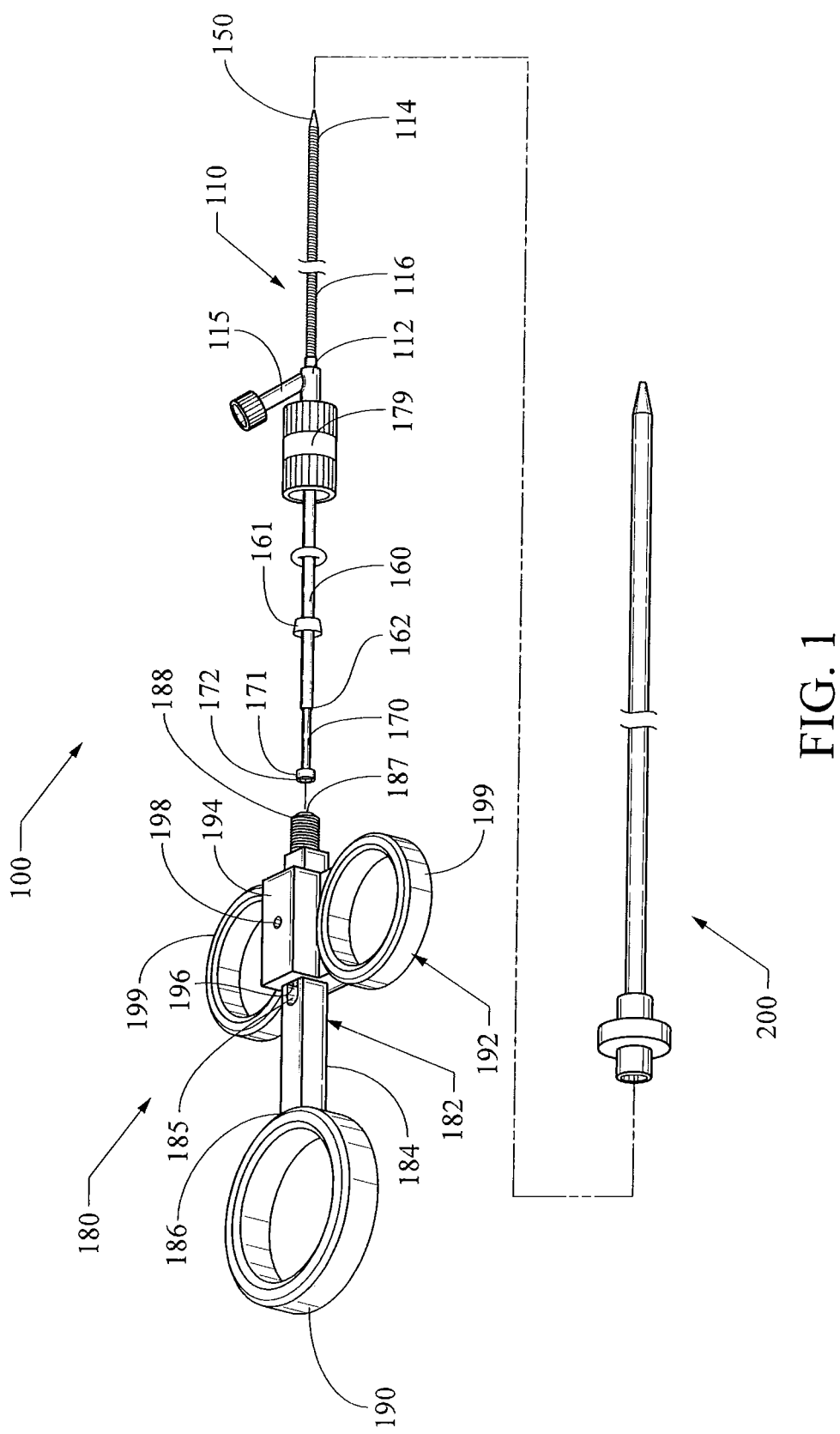
FIG. 1 is a perspective view of one example of a needle system.

For the purposes of promoting an understanding of the principles of the present disclosure, reference will now be made to the embodiments illustrated in the drawings, and specific language will be used to describe the same.

In the following discussion, the terms "proximal" and "distal" will be used to describe the opposing axial ends of a medical instrument or device, as well as the axial ends of various component features. The term "proximal" is used in its conventional sense to refer to the end of the instrument (or component thereof) that is closest to the operator during use of the instrument. The term "distal" is used in its conventional sense to refer to the end of the instrument (or component thereof) that is initially inserted into the patient, or that is closest to the patient during use.

Generally speaking, the present disclosure is directed to a medical instrument. The instrument may be used to puncture the interatrial septum between the left and right atria of the heart. The medical instrument may be a needle system including a needle and a catheter. The needle may be received within the catheter as further described below for delivery to a desired location within the body of a patient.

Figure 2A:
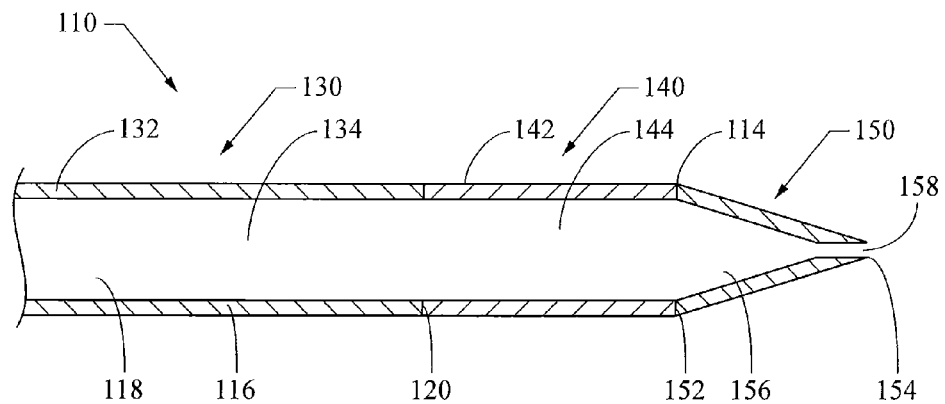
FIG. 2A is a partial longitudinal cross sectional view of a distal portion of one embodiment of a needle.
Figure 2B:
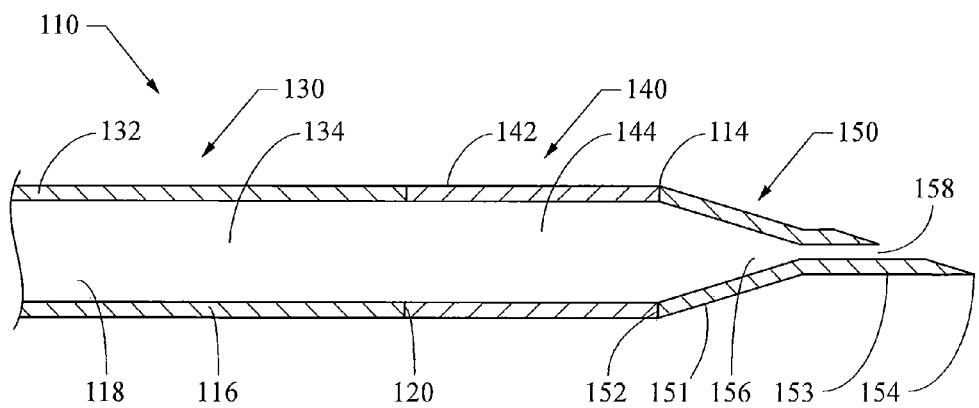
FIG. 2B is a partial longitudinal cross sectional view of a distal portion of another embodiment of a needle.
Figure 3:
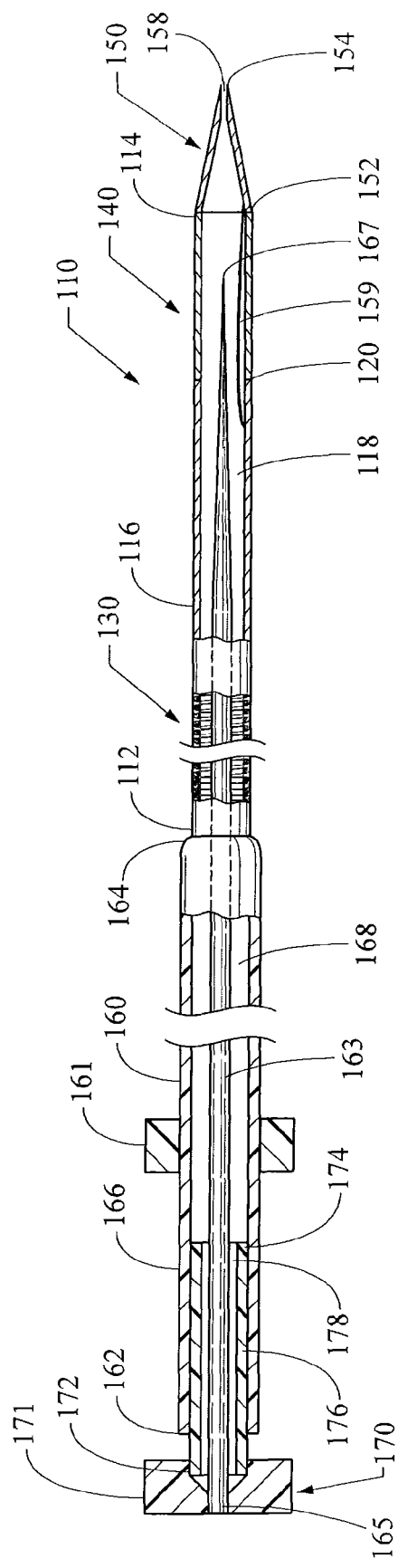
FIG. 3 is a partial longitudinal cross sectional view of a distal portion of a needle including an actuating system.

FIGS. 1-3 depict one example of a needle system including a needle 100 and a catheter 200. The needle 100 may be a tip deflecting needle configured for transseptal puncture as further described below. The needle 100 may include a cannula 110. A needle tip 150 may be attached to the distal end of the cannula 110. An actuating system, which may include a fixed tube 160 and a movable tube 170, may be attached to the proximal end of the cannula 110. A proximal manipulation portion such as a handle 180 may be positioned at the proximal end of the needle 100 for actuating the actuating system as further described below.

The cannula 110 may be configured as an elongate tubular member having a proximal end 112 and a distal end 114. An outer wall 116 of the cannula 110 may define a cannula lumen 118 extending within the cannula between the proximal end 112 and the distal end 114 of the cannula. A side port 115 may extend from the cannula 110 near the proximal end of the cannula. A lumen of the side port 115 may be in fluid communication with the lumen 118 of the cannula 110. The side port may include a conventional connector (e.g., a Luer lock connector) for attaching a syringe or other medical instrument to the side port. Alternatively, or additionally, the side port 115 may extend from the fixed tube 160 (described below) of the actuating system of the needle 100, and the lumen of the side port may be in fluid communication with the lumen of the fixed tube. The side port 115 may be used to introduce a contrast fluid or other therapeutic agent into the lumen 118 of the cannula 110 and out through a distal end opening of the needle tip 150. A pressure measurement device may be attached to the side port 115 to measure the pressure within the lumen 118. The pressure measurement device may be used to determine an atrial pressure as further described below. The cannula may have a length in the range of about 40 to about 300 cm, and preferably in the range of about 40 to about 80 cm. The cannula may have an inner diameter in the range of about 0.204 to about 1.072 mm (about 0.008 to about 0.042 in). The cannula may have an outer diameter in the range of about 0.330 to about 1.486 mm (about 0.0130 to about 0.0585 in). The distal end 114 of the cannula 110 may be swaged or otherwise tapered to conform to a diameter of the needle tip 150 and to aid in advancing the needle 100 within the vasculature of the patient or through the interatrial septum as further described below.

As shown in FIG. 2A, the cannula 110 may include a first segment 130 and a second segment 140. Each of the first and second segments may have any suitable length. In one example, the first segment 130 may have a length ranging from about 30 to about 45 cm, and the second segment 140 may have a length ranging from about 20 to about 35 cm. The first segment 130 of the cannula 110 may extend longitudinally between the proximal end 112 and an intermediate point 120 of the cannula. The first segment 130 may be configured as a flexible tubular member capable of being passed through tortuous anatomy as further described below. The first segment 130 of the cannula 110 may include an outer wall 132 defining a lumen 134 extending generally longitudinally within the first segment. The outer wall 132 of the first segment 130 may be generally longitudinally incompressible. In other words, the outer wall 132 of the first segment 130 may not substantially compress longitudinally upon application of a force on the first segment in the longitudinal direction. In one example, the outer wall 132 may be configured as a substantially solid wall as shown in FIG. 2A. In another example, the outer wall 132 may be configured as a coil as further described below.

The second segment 140 of the cannula 110 may extend longitudinally between the intermediate point 120 and the distal end 114 of the cannula. The second segment 140 may be attached to the first segment 130 at the intermediate point 120 of the cannula. For example, the first segment 130 and the second segment 140 may be attached to one another by a solder, a weld, a braze, or any other suitable attachment. Alternatively, the first segment 130 and the second segment 140 may be integrally formed as a unitary structure. The second segment 140 may be configured as a flexible tubular member capable of being passed through tortuous anatomy as further described below. The second segment 140 of the cannula 110 may include an outer wall 142 defining a lumen 144 extending generally longitudinally within the second segment. The lumen 134 of the first segment 130 and the lumen 144 of the second segment 140 may be in fluid communication with one another to cooperatively form the lumen 118 of the cannula 110. At least a portion of the outer wall 142 of the second segment 140 may be longitudinally compressible. In other words, at least a portion of the outer wall 142 of the second segment 140 may compress longitudinally upon application of a force on the second segment in the longitudinal direction as further described below.

The needle 100 also may include a needle tip 150 as shown in FIGS. 1-3. The needle tip 150 may extend from the distal end 114 of the cannula 110 to form a distal tip of the needle 100. The needle tip 150 may be attached to the cannula 110 by a solder, a weld, a braze, or any other suitable attachment. Preferably, the attachment between the needle tip 150 and the cannula 110 may be ground or polished to form a smooth outer surface to avoid damaging a body vessel into which the needle 100 may be introduced. The smooth outer surface of the cannula 110 also may aid in introducing the cannula within the catheter 200.

The needle tip 150 may include a proximal end 152, a distal end 154, and a needle lumen 156 extending between the proximal and distal ends of the needle tip. The needle lumen 156 may be in fluid communication with the lumen 118 of the cannula 110. The needle tip 150 also may include a distal end opening 158 which may be in fluid communication with the needle lumen 156. A material such as a contrast fluid or therapeutic agent may be passed through the lumen 118 of the cannula, into the needle lumen 156, and out through the distal end opening 158 of the needle tip 150. The distal end 154 of the needle tip 150 may be configured to puncture body tissue as further described below. To that end, the distal end 154 may be beveled, pointed or otherwise sharpened.

In one example, the needle tip 150 may include a tapered segment 151, a straight segment 153, and a beveled tip as shown in FIG. 2B. The tapered segment 151 may be configured as a transition from the cannula 110 to the straight segment 153 of the needle tip 150. To that end, the diameter of the tapered segment 151 may taper from the diameter of the cannula 110 to the diameter of the straight segment 153. The diameter of the straight segment 153 of the needle tip 150 may be less than the diameter of the cannula 110. The straight segment 153 of the needle tip 150 may have a longer length at a first circumferential position than at a second circumferential position opposite the first circumferential position to form the beveled distal end 154 as shown in FIG. 2B. The straight segment 153 and/or the beveled distal end 154 may aid in piercing body tissue as further described below.

A safety wire 159 may be attached to the needle tip 150 near the proximal end 152 of the needle tip as shown in FIG. 3. The safety wire may extend within the lumen 118 of the cannula 110 and may be attached to an inner surface of the outer wall 116 of the cannula. The safety wire 159 may couple the needle tip 154 to the cannula 110 to prevent the needle tip from loosening or otherwise separating from the cannula. The safety wire 159 also may aid in movement or deflection of the second segment 140 of the cannula 110 relative to the first segment 130 of the cannula as described below. The safety wire 159 may be configured to resist longitudinal compression. Upon application of a compressive force to the second segment 140 of the cannula 110 as described above, a portion of the second segment adjacent the safety wire 159 may be substantially unable to compress. Thus, a portion of the second segment 140 generally opposite the safety wire 159 may compress while the portion of the second segment adjacent the safety wire remains substantially uncompressed. This unbalanced compression of the second segment 140 of the cannula 110 may cause the second segment to deflect relative to the first segment of the cannula in a direction generally away from the safety wire 159 as described below.

The needle tip 150 also may include one or more surface features to enable visualization of the needle tip during use of the needle tip within the vasculature of the patient as further described below. For example, the distal end 154 of the needle tip 150 may be roughened, textured, or dimpled to enable visualization of the needle tip by ultrasound. In one example, the needle tip 150 and/or the surface features of the needle tip may be formed from a radiopaque material for visualization by fluoroscopy. In other examples, the needle tip 150 or a portion thereof may be configured for visualization by x-ray, tomography, magnetic resonance imaging, or any other visualization technique.

The needle 100 also may include an actuating system including a fixed tube 160 and a movable tube 170 as shown in FIGS. 1 and 3. The fixed tube 160 and the movable tube 170 may cooperate to move or deflect the second segment 140 of the cannula 110 relative to the first segment 130 of the cannula as further described below. The fixed tube 160 may be configured as an elongate tubular member having a proximal end 162 and a distal end 164. An outer wall 166 of the fixed tube 160 may define a lumen 168 extending generally longitudinally within the fixed tube between the proximal end 162 and the distal end 164 of the fixed tube. The distal end 164 of the fixed tube 160 may be attached to the proximal end 112 of the cannula 110 such that the lumen 168 of the fixed tube may be in fluid communication with the lumen 118 of the cannula. The fixed tube 160 and the first segment 130 of the cannula 110 may be substantially coaxial. The fixed tube 160 may include a flange 161 positioned on an outer surface of the outer wall 166 of the fixed tube between the proximal end 162 and the distal end 164 of the fixed tube. The flange 161 may be configured to engage the handle of the needle as further described below.

The movable tube 170 may be configured as an elongate tubular member having a proximal end 172 and a distal end 174. An outer wall 176 of the movable tube 170 may define a lumen 178 extending generally longitudinally within the movable tube between the proximal end 172 and the distal end 174 of the movable tube. The lumen 178 may extend along a distal portion of the length of the movable tube 170. For example, the lumen 178 may extend between the distal end 174 of the movable tube and a point near the proximal end 172 of the movable tube as shown in FIG. 3. In this example, the distal end 174 of the movable tube 170 may include an end opening in communication with the lumen 178, while the proximal end 172 of the movable tube may be configured as a closed end. At least a portion of the movable tube 170 may be received within the lumen 168 of the fixed tube 160 such that the fixed tube and the movable tube may be substantially coaxial. The movable tube 170 may be configured to slide longitudinally within the lumen 168 of the fixed tube 160 to move or deflect the second segment 140 of the cannula 110 relative to the first segment 130 of the cannula as further described below. The lumen 178 of the movable tube 170 may be in fluid communication with the lumen 168 of the fixed tube 160. The movable tube 170 also may include a flange 171 positioned on an outer surface of the outer wall 176 of the movable tube. The flange 171 may be positioned at the proximal end 172 of the movable tube 170 to engage the handle of the needle as further described below.

A mandril wire 163 may extend generally longitudinally within the lumen 178 of the movable tube 170, the lumen 168 of the fixed tube 160, and the lumen 118 of the cannula 110. In the example shown in FIG. 3, a proximal end 165 of the mandril wire 163 may be received within the lumen 178 of the movable tube 170. The proximal end 165 of the mandril wire 163 may be fixedly attached to the movable tube 170. For example, the proximal end 165 of the mandril wire 163 may be fixedly attached to an inner surface of the outer wall 176 of the movable tube 170. Additionally, or alternatively, the proximal end 165 of the mandril wire 163 may be fixedly attached to the flange 171 at the proximal end 172 of the movable tube 170. A distal end 167 of the mandril wire 163 may be fixedly attached to the cannula 110 near the distal end 114 of the cannula 110. For example, the distal end 167 of the mandril wire 163 may be fixedly attached to an inner surface of the outer wall 116 of the cannula 110 near the distal end 114 of the cannula. Additionally, or alternatively, the distal end 167 of the mandril wire 163 may be fixedly attached to the needle tip 150 or a cap positioned at the distal end 114 of the cannula 110. Such a cap may include an orifice so that the needle tip 150 may be in fluid communication with the lumen 118 of the cannula 110 through the orifice of the cap. The mandril wire 163 may be configured such that longitudinal movement of the mandril wire relative to the cannula 110 may cause the second segment 140 of the cannula 110 to move or deflect relative to the first segment 130 of the cannula as further described below.

The mandril wire 163 may be configured as any conventional wire known in the art. For example, the mandril wire 163 may be a wire having a rectangular (or flat), round, or any other shape cross section. A tubular member (e.g., a tapered cannula) may be used instead of or in addition to the mandril wire 163. For example, a proximal end of the tubular member may be fixedly attached to the movable tube 170, and a distal end of the tubular member may be fixedly attached near the distal end 114 of the cannula 110. Longitudinal movement of the tubular member may cause deflection of the second segment 140 of the cannula 110 as described below.

The needle 100 also may include a proximal manipulation portion such as a handle 180. The handle 180 may be configured to remain substantially external to the body of the patient during use of the medical instrument. The handle 180 may be configured as a three-ring handle as shown in FIG. 1. To that end, the handle 180 may include a fixed portion 182 and a movable portion 192.

The fixed portion 182 of the handle 180 may include a shaft 184 having a proximal end 186 and a distal end 188. The shaft 184 may be configured as an elongate member having a substantially square shaped cross section as shown in FIG. 1. Alternatively, the cross section of the shaft 184 may have a rectangular, triangular, circular, or any other polygonal or non-polygonal shape. The fixed portion 182 also may include a ring 190 attached to the proximal end 186 of the shaft 184. The ring 190 may be a substantially circular member configured to receive a thumb of a physician during operation of the medical instrument.

A slot 185 may be formed through the shaft 184. The slot 185 may extend entirely through the shaft 184 between opposing top and bottom surfaces of the shaft. Alternatively, the slot 185 may extend between opposing side surfaces of the shaft. The slot 185 also may extend substantially longitudinally along at least a portion of the length of the shaft 184. The slot 185 may be configured to engage the movable portion 192 of the handle 180 as further described below. A bore 187 also may be formed within the shaft 184. The bore 187 may extend generally longitudinally within the shaft between the slot 185 and the distal end 188 of the shaft. In other words, the bore 187 may be in communication with the slot 185.

The movable portion 192 of the handle 180 may include a block 194. The block 194 may be positioned around at least a portion of the shaft 184 of the fixed portion 182 of the handle 180. To that end, the block 194 may include a passage 196 extending generally longitudinally within the block. The passage 196 may be sized and shaped to receive the shaft 184 of the fixed portion 182 of the handle 180. For example, the passage 196 may have a substantially square shaped cross section to correspond to the cross section of the shaft 184 as described above. The block 194 may include a pin 198 that may traverse the passage 196 of the block. With the shaft 184 received within the opening 196, the pin 198 may be received within the slot 185 of the shaft. The block 194 may be longitudinally movable relative to the shaft 184. Upon longitudinal movement of the block 194 relative to the shaft 184, the pin 198 may move longitudinally within the slot 185. The movable portion 192 also may include one or more rings 199. For example, a pair of rings 199 may be attached to opposing sides of the block 194 as shown in FIG. 1. The rings 199 may be substantially circular members, each configured to receive a finger of a physician during operation of the medical instrument. The ring 190 and the rings 199 may be substantially coplanar. By placing the respective fingers (e.g., the thumb, index finger, and middle finger) in the respective rings 190, 199, the physician may be capable of moving the block 194 longitudinally with respect to the shaft 184. In this manner, the physician may be capable of moving the block 194 longitudinally with respect to the shaft 184 using only one hand. In other words, the three-ring handle described above may be suitable to enable one-handed operation of the medical instrument.

The proximal end 172 of the movable tube 170 may be received within the bore 187 of the shaft 184 of the fixed portion 182 of the handle 180. The proximal end 162 of the fixed tube 160 also may be received within the bore 187. A sufficient portion of the fixed tube 160 may be received within the bore 187 so that the flange 161 of the fixed tube 160 may be in abutting contact with the distal end 188 of the shaft 184. The fixed tube 160 may be attached to the shaft 184 with a retainer 179. For example, the retainer 179 may engage the flange 161 of the fixed tube 160 and the shaft 184 to retain the flange in abutting contact with the shaft. The proximal end 172 of the movable tube 170 may be extended proximally of the proximal end 162 of the fixed tube 160 so that at least a portion of the movable tube may be positioned within the slot 185 formed in the shaft 184. The movable portion 192 of the handle 180 may engaged the movable tube 170. For example, a portion of the block 194 positioned within the slot 185 may engage the flange 171 of the movable tube 170. In other words, the flange 171 may be positioned within the slot 185 formed in the shaft 184 to be engaged by a portion of the block 194. In this manner, the movable tube 170 may be fixedly attached to the movable portion 192 of the handle 180. Longitudinal movement of the movable portion 192 of the handle 180 relative to the fixed portion 182 of the handle may cause a corresponding longitudinal movement of the movable tube 170 relative to the fixed tube 160. Such movement also may cause longitudinal movement of the mandril wire 163 (which is fixedly attached to the movable tube 170) relative to the cannula 110 to move or deflect the second segment 140 of the cannula relative to the first segment 130 of the cannula as further described below.

Figure 4:
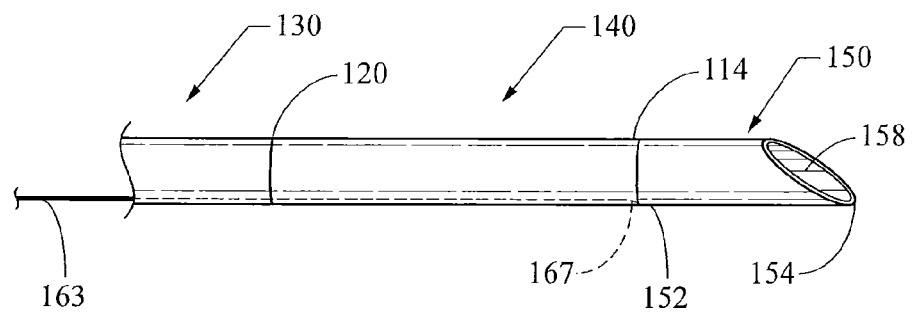
FIG. 4 depicts a distal portion of a needle with a segment of the needle in a neutral configuration.
Figure 5:
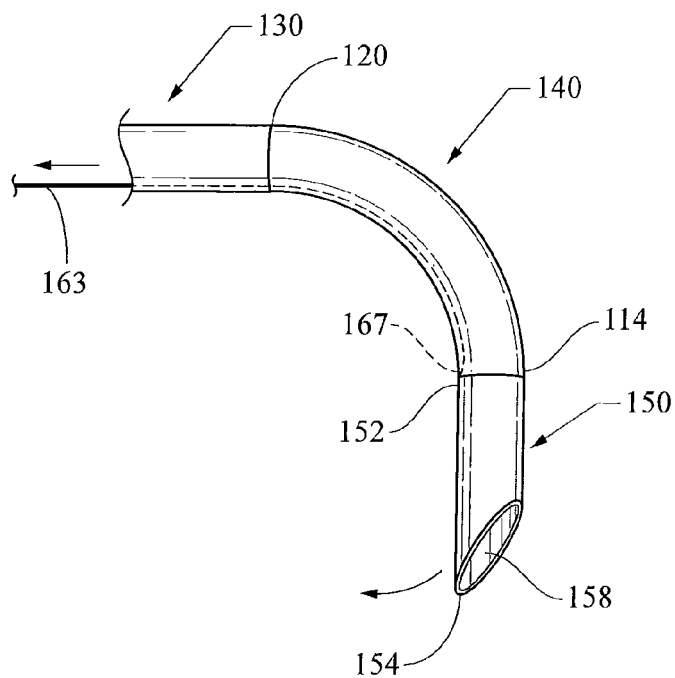
FIG. 5 depicts a distal portion of a needle with a segment of the needle in a deflected configuration.

FIGS. 4-5 illustrate the deflection of the second segment 140 of the cannula 110 relative to the first segment 130 of the cannula. FIG. 4 shows the second segment 140 of the cannula 110 in a neutral configuration. In the neutral configuration, the longitudinal axis of the second segment 140 may be substantially linear. In other words, the second segment 140 of the cannula 110 in the neutral configuration may extend in a substantially straight line from the intermediate point 120 of the cannula. FIG. 5 shows the second segment 140 of the cannula 110 in a deflected configuration. In the deflected configuration, the longitudinal axis of the second segment 140 may be curved. In other words, the second segment 140 of the cannula 110 in the deflected configuration may extend from the intermediate point 120 of the cannula in a curved or arcuate fashion. The second segment 140 of the cannula 110 may be deflected up to about 180 degrees relative to the first segment 130 of the cannula such that the distal end opening 158 of the needle tip 150 may be directed generally proximally with respect to the longitudinal axis of the first segment 130 of the cannula. Generally, the second segment 140 may be deflected up to about 90 degrees with respect to the first segment 130 of the cannula 110 as shown in FIG. 5. The second segment 140 of the cannula may be placed in the neutral configuration, the deflected configuration, or any other orientation between the neutral configuration and the deflected configuration. In other words, the second segment 140 may be deflected relative to the first segment 130 of the cannula 110 to any angle up to a maximum angle of deflection.

The second segment 140 of the cannula 110 may be deflected by longitudinal movement of the mandril wire 163 relative to the cannula 110. For example, at least a portion of the second segment 140 of the cannula 110 may be longitudinally compressible. More specifically, at least a circumferential segment of the outer wall 142 of the second segment 140 may be longitudinally compressible. The compressible segment may extend longitudinally along substantially an entire length of the second segment 140 of the cannula 110. The mandril wire 163 may be positioned within the lumen 144 of the second segment 140 of the cannula 110 and generally aligned with the compressible circumferential portion of the second segment of the cannula. In one example, the mandril wire 163 may be in contact with the compressible circumferential portion of the second segment 140 of the cannula along the inner surface of the outer wall 142.

The mandril wire 163 may be retracted longitudinally in a proximal direction relative to the cannula 110 by manipulating the handle 180 as described above. Longitudinal retraction of the mandril wire 163 in the proximal direction may exert a longitudinal force on the compressible circumferential portion of the second segment 140 of the cannula. This longitudinal force may cause the compressible circumferential portion of the cannula 110 to compress longitudinally. As described above, a portion of the second segment 140 of the cannula 110 adjacent the safety wire 159 may be substantially unable to compress because the safety wire may resist such compression. A portion of the second segment 140 generally opposite the safety wire 159 may compress longitudinally. Thus, one circumferential portion of the second segment 140 of the cannula 110 (e.g., the portion generally opposite the safety wire 159) may compress longitudinally by a greater amount than another circumferential portion of the second segment (e.g., the portion adjacent the safety wire 159). The length of the compressible portion of the cannula 110 may be reduced upon such compression, which may cause the second segment 140 of the cannula to deflect in the direction of the compressible portion of the cannula as shown in FIG. 5. Further retraction of the mandril wire in the proximal direction may cause further compression of the compressible portion of the cannula 110 and, thus, further deflection of the second segment 140 of the cannula. Conversely, advancement of the mandril wire 163 in the distal direction relative to the cannula 110 may cause the second segment 140 of the cannula to move toward the neutral configuration from the deflected configuration. In one example, further advancement of the mandril wire 163 in the distal direction with the second segment 140 of the cannula 110 in the neutral configuration may cause the compressible portion of the second segment to expand and the second segment to deflect in the opposite direction of the deflected configuration shown in FIG. 5. However, such expansion of the compressible portion may be limited by the safety wire 159.

By retracting or advancing the mandril wire 163 relative to the cannula 110 (e.g., by manipulating the handle 180), the amount of deflection of the second segment 140 of the cannula 110 may be controlled. Thus, the orientation of the needle tip 150, which is attached to the distal end 114 of the cannula 110, relative to the first segment 130 of the cannula also may be controlled. As further described below, the ability to control the orientation of the needle tip 150 relative to the first segment 130 of the cannula 110 may enable the needle tip to be directed at a precise location within a patient's body. The ability to control the orientation of the needle tip 150 by deflecting a portion of the needle 100, as opposed to a portion of the catheter 200, may reduce the complexity of operating the needle system.

Figure 6:
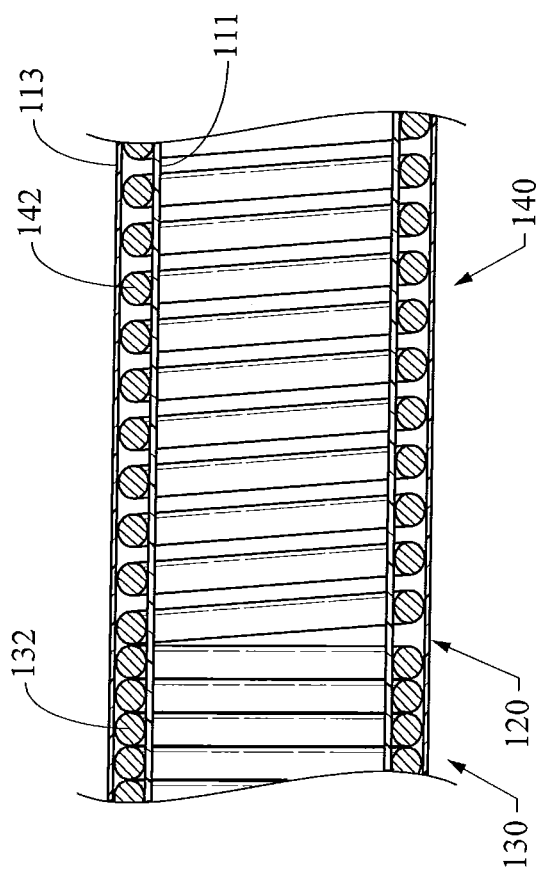
FIG. 6 is a partial longitudinal cross sectional view of an intermediate segment of a needle.

The outer wall 116 of the cannula 110 may be formed from a substantially solid tube as shown in FIGS. 2A-2B. Alternatively, the outer wall 116 may be formed from a coil as shown in FIG. 6. The coil may be formed from well-known materials for such use in the medical arts, such as a metal, a metal alloy (e.g., stainless steel or a shape memory composition such as nitinol), a multi-filar material, or a composite material. In one example, the coil may be formed from a wire having a substantially circular cross sectional shape as shown in FIG. 6. In other examples, a low profile coil, such as a coil having a conventional flat wire construction, may be used to minimize the cross sectional profile (i.e., outer diameter) of the cannula 110. Alternatively, the coil may have a different cross sectional shape such as oval, or any other geometric shape. The coil may be formed using any known technique including, for example, wrapping one or more wires around a mandrel.

The spacing between the individual windings of the coil may be configured to impart a desired compressibility to the outer wall 116. For example, the windings of the coil that forms the outer wall 132 of the first segment 130 of the cannula 110 may be configured such that the first segment of the cannula is substantially longitudinally incompressible. To that end, each winding of the first segment 130 may be in abutting contact with an adjacent winding of the first segment as shown in FIG. 6. In other words, adjacent windings of the first segment 130 of the cannula 110 may not be substantially spaced from one another. Thus, upon application of a longitudinal force to the outer wall 132 of the first segment 130, the windings may be unable to move closer together, and the outer wall 132 may be substantially longitudinally incompressible. Conversely, the windings of the coil that forms the outer wall 142 of the second segment 140 of the cannula 110 may be configured such that the second segment of the cannula is longitudinally compressible. To that end, each winding of the second segment 140 may be spaced from an adjacent winding of the second segment. In other words, adjacent windings of the second segment 140 of the cannula 110 may be spaced from one another. Thus, upon application of a longitudinal force to the outer wall 142 of the second segment 140, the windings may be able to move closer together (i.e., the lengths of the spaces between the windings may be reduced), and the outer wall 142 may be longitudinally compressible.

The outer wall 116 of the cannula 110 may be formed of a single, unitary coil structure. The spacing between the windings of the portion of the coil structure that forms the outer wall 132 of the first segment 130 of the cannula 110 may be different (e.g., smaller) than the spacing between the windings of the portion of the coil structure that forms the outer wall 142 of the second segment 140 of the cannula. In this manner, the longitudinal compressibility of each of the first segment 130 and the second segment 140 of the cannula 110 may be controlled as described above.

In another example, the outer wall 116 of the cannula 110 may be formed from separate coil structures joined to one another at the intermediate point 120. One coil structure may form the outer wall 132 of the first segment 130 of the cannula 110. The spacing between the windings of this coil structure may be configured such that the outer wall 132 is substantially longitudinally incompressible as described above. Another coil structure may form the outer wall 142 of the second segment 140 of the cannula 110. The spacing between the windings of this coil structure may be configured such that at least a portion of the outer wall 142 is longitudinally compressible also as described above. The two coil structures may be attached by any suitable means. Preferably, the joint between the two coil structures may be ground or polished so that the joint is substantially smooth to reduce the potential for damage to the vasculature of the patient upon introduction of the cannula 110 within the vasculature as further described below.

An inner liner 111 may be positioned within the lumen 118 of the cannula 110 as shown in FIG. 6. Although the inner liner 111 is shown within the lumen of a coil structure defining the wall 116 of the cannula 110, an inner liner also may be included within the lumen of a solid cannula wall as described above. The inner liner 111 may be configured as a generally tubular member having a lumen extending generally longitudinally therein. For example, the inner liner 111 may be a length of tubing sized to generally conform to the inner surface of the outer wall 116 of the cannula 110. The inner liner 111 may be formed from any material known in the art. For example, the inner liner 111 may be formed from a polymeric material such as a polyether block amide, nylon, polyurethane, polytetrafluoroethylene (PTFE), polyether ether ketone (PEEK), or any other suitable polymeric or non-polymeric material. The inner liner 111 may extend along at least a portion of the length of the cannula 110 between the proximal end 112 and the distal end 114 of the cannula. A substantially continuous flow pathway may be formed within the lumen of the inner liner 111 to aid introduction of contrast fluid or therapeutic agents within the lumen 118 of the cannula 110 and/or measurement of the pressure at the distal end opening 158 of the needle tip 150 as further described below.

An outer layer such as a polymeric jacket 113 also may be positioned substantially surrounding an outer surface of the outer wall 116 of the cannula 110. The jacket 113 may be formed from any suitable material known in the art. Preferably, the jacket 113 may be formed from a conventional lubricious material such as, for example, polytetrafluoroethylene (PTFE), fluorinated ethylene propylene (FEP), or another fluoropolymer material. The lubricious material may provide a slippery, low friction outer surface to ease insertion and/or withdrawal of the needle 100 within the catheter 200 as described herein. To that end, the jacket 113 may extend generally longitudinally along at least a portion of the length of the cannula 110 between the proximal end 112 and the distal end 114 of the cannula.

Figure 7:
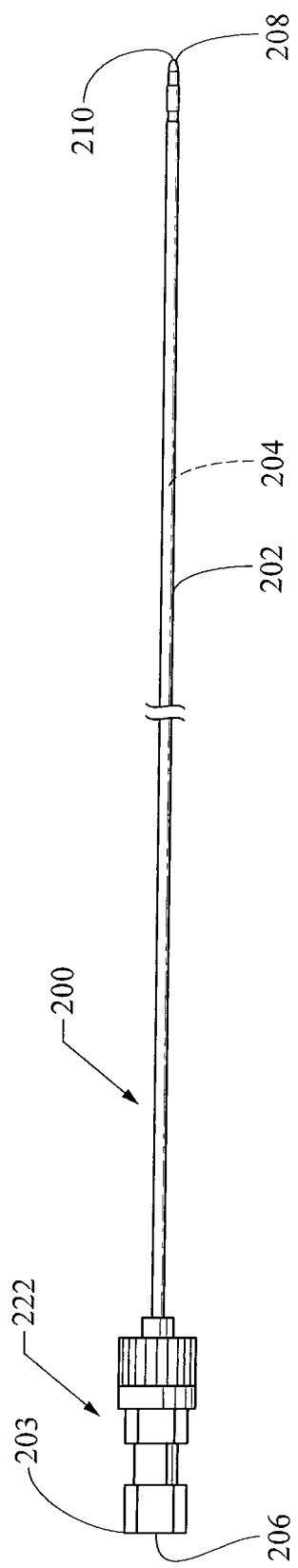
FIG. 7 is a perspective view of one example of a catheter.

The needle 100 may be provided as part of a needle system which also may include a catheter 200 as shown in FIG. 7. The catheter 200 may include an elongate tube 202 having an open central lumen 204 extending therethrough. The tube 202 may be made from any flexible, biologically compatible material such as polyurethane. The proximal end 203 of the tube 202 may include an opening 206, which may be in fluid communication with the lumen 204. A flange 222 may be positioned at the proximal end of the tube 202 to receive at least a portion of the needle 100 as further described below. The distal end 208 of the tube 202 may be tapered and may include an axially directed end hole 210. The end hole 210 may be in fluid communication with the lumen 204 of the tube 202. The tapered distal end 208 may enable the catheter 200 to dilate and transition through a puncture point in a body tissue as further described below. To that end, the tapered distal end 208 may include a thin wall portion. The catheter 200 also may be configured to enable visualization of the catheter using any known visualization technique (e.g., x-ray, tomography, magnetic resonance imaging, ultrasound, fluoroscopy, or any other visualization technique) during navigation of the catheter within the vasculature of the patient. For example, the distal end 208 of the catheter 200 may include one or more radiopaque markers to enable visualization of the distal end 208 by fluoroscopy.

Figure 8:
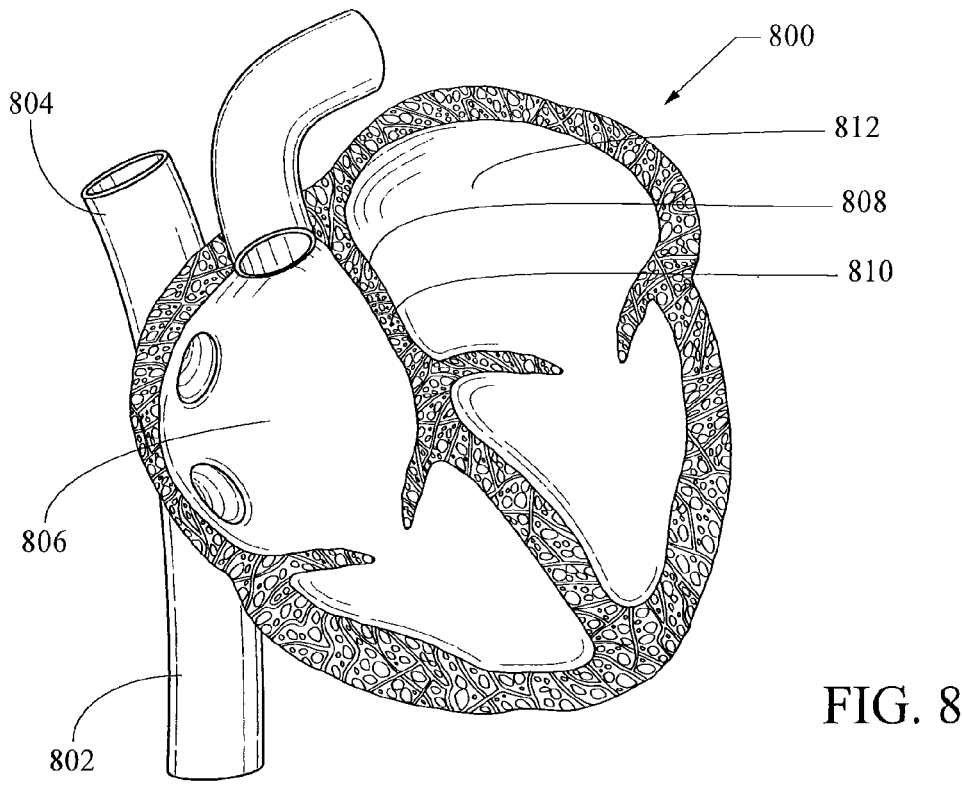
FIG. 8 is a diagrammatic cross sectional view of a heart of a patient.

FIGS. 8-13 illustrate an exemplary method of puncturing an interatrial septum using the needle system described above. FIG. 8 illustrates a cutaway view of a heart 800 of a patient. An inferior vena cava 802 and a superior vena cava 804 are attached to and in fluid communication with a right atrium 806 of the heart 800. Blood generally may flow from the inferior vena cava 802 and the superior vena cava 804 into the right atrium 806. The heart 800 also includes a left atrium 812 which is separated from the right atrium 806 by an interatrial septum 808. The interatrial septum 808 includes a fossa ovalis 810, which may be a suitable point at which to puncture the interatrial septum 808 as further described below. A medical instrument, such as a catheter or needle, introduced into the right atrium 806 via the inferior vena cava 802 may be directed generally toward the superior vena cava 804 as opposed to the interatrial septum 808. In other words, the medical instrument may not tend to align with the interatrial septum 808 upon introduction into the right atrium 806 via the inferior vena cava 802. This may add to the difficulty of directing the medical instrument toward the interatrial septum 808 to puncture the interatrial septum at a precise location thereon.

The cannula 110 of the needle 100 may be inserted within the lumen 204 of the catheter 200 as described above. The cannula 110 may be positioned within the lumen 204 such that the distal end 154 of the needle tip 150 may be positioned within the lumen of the catheter 200. In other words, the needle tip 150 may not extend beyond the distal end 208 of the catheter 200. Such positioning may reduce the potential for the needle tip 150 to inadvertently puncture a portion of the vasculature during introduction and navigation of the needle system within the patient's body.

Figure 9:
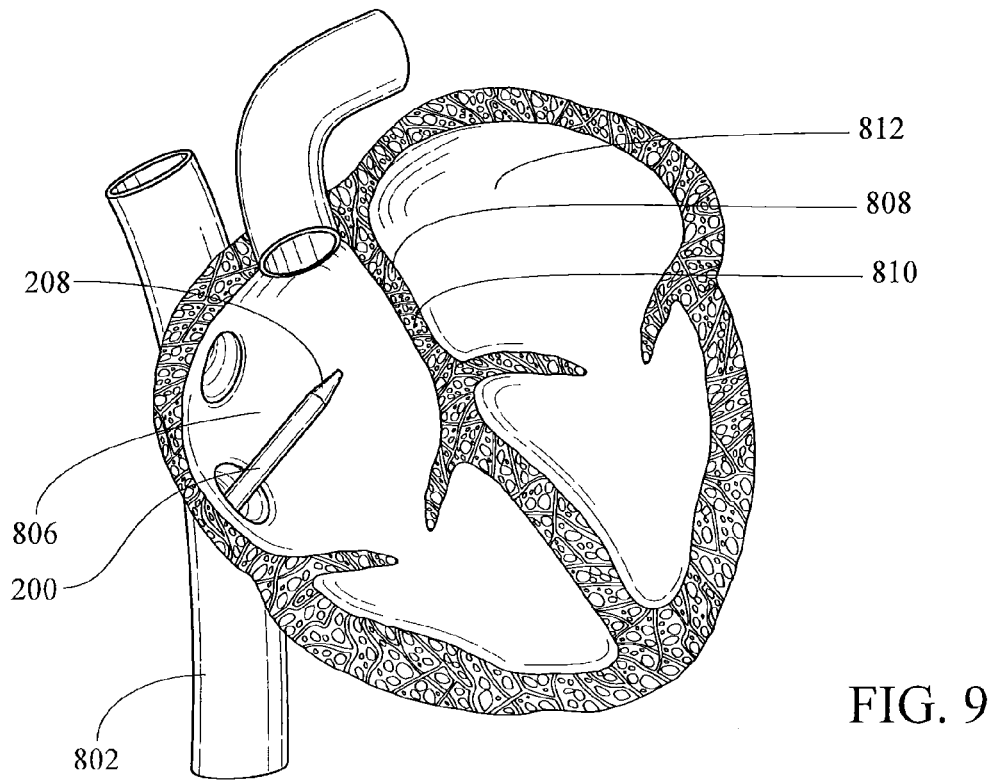
FIG. 9 illustrates a distal portion of a catheter positioned within a right atrium of the heart of FIG. 8.

The catheter 200, with the cannula 110 of the needle 100 received therein, may be introduced into the right femoral vein using any conventional endovascular technique. The catheter 200 and the needle 100 may be advanced within the vasculature of the patient and navigated to the inferior vena cava 802. The distal end 208 of the catheter 200 may be visualized during navigation of the catheter and the needle 100 within the vasculature of the patient using any visualization technique as described above. The catheter 200 and the needle 100 may be further advanced until the distal end 208 of the catheter is positioned within the right atrium 806 as shown in FIG. 9. The needle lumen 156 of the needle tip 150 (which may be positioned within the catheter 200) may be in fluid communication with the right atrium 806 via the distal end opening 158 of the needle tip. Thus, the lumen 118 of the cannula 110 also may be in fluid communication with the right atrium 806. A right atrial pressure may be determined by measuring the pressure within the lumen 118 of the cannula 110 via the side port 115. The right atrial pressure may be used by the physician to confirm that the distal end 208 of the catheter 200 is properly positioned within the right atrium. The position of the distal end 208 of the catheter 200 also may be confirmed via any suitable visualization technique.

Figure 10:
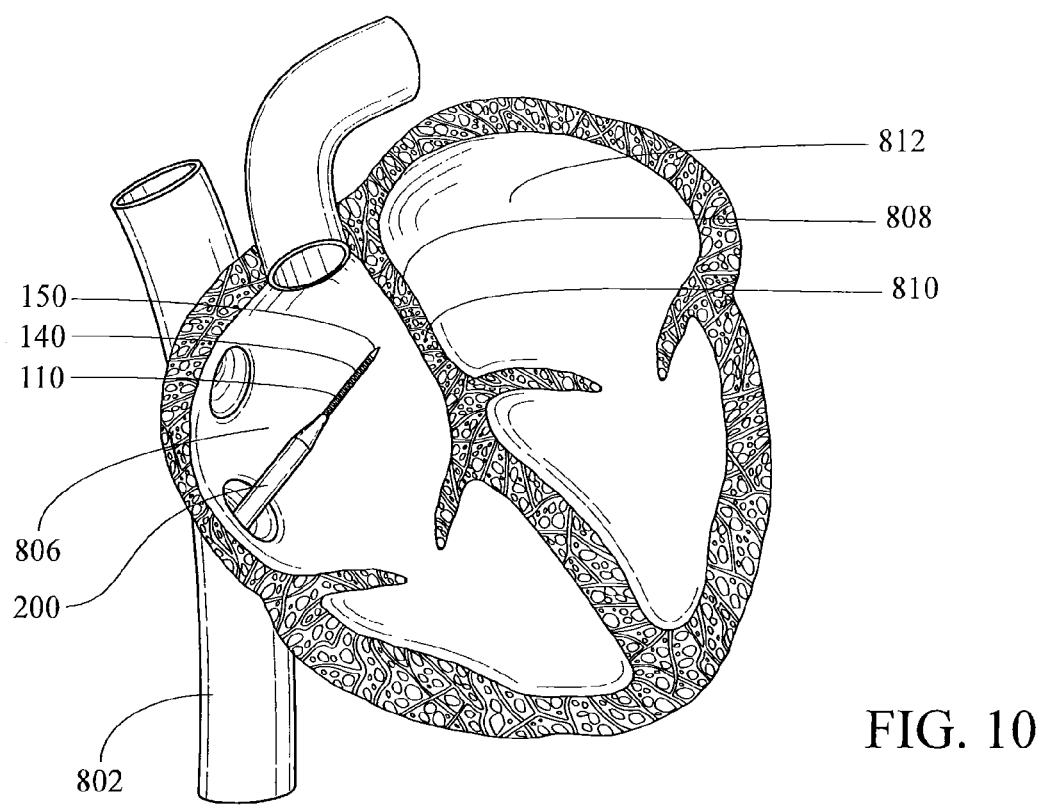
FIG. 10 illustrates a distal portion of a catheter and a distal portion of a needle in a neutral configuration positioned within a right atrium of the heart of FIG. 8.

Upon confirming that the catheter 200 is positioned within the right atrium 806 as desired, the catheter 200 may be retracted proximally relative to the needle 100 to expose at least a portion of the needle 100. For example, the catheter 200 may be retracted a sufficient distance to expose the needle tip 150 and the second segment 140 of the cannula 110 as shown in FIG. 10. The needle tip 150 may be directed generally in the direction of the interatrial septum 808. However, the needle tip 150 may not be aligned with a desired location at which to puncture the interatrial septum (e.g., the fossa ovalis 810). In other words, the needle tip 150 may be misaligned with the desired puncture point. Puncturing the interatrial septum at the desired point may be important to avoid inadvertently advancing the needle tip 150 into a location other than the left atrium (e.g., the aorta). Puncturing the interatrial septum at the fossa ovalis may be beneficial because the fossa ovalis may be a relatively thin portion of the interatrial septum which may be relatively easy to puncture. Additionally, physicians may be able to place devices (e.g., valves, mitrial clips, or other devices) and perform valvoplasties or other procedures percutaneously. Precise placement of the puncture on the interatrial septum may enable the physician to properly place such devices or perform such procedures.

Figure 11:
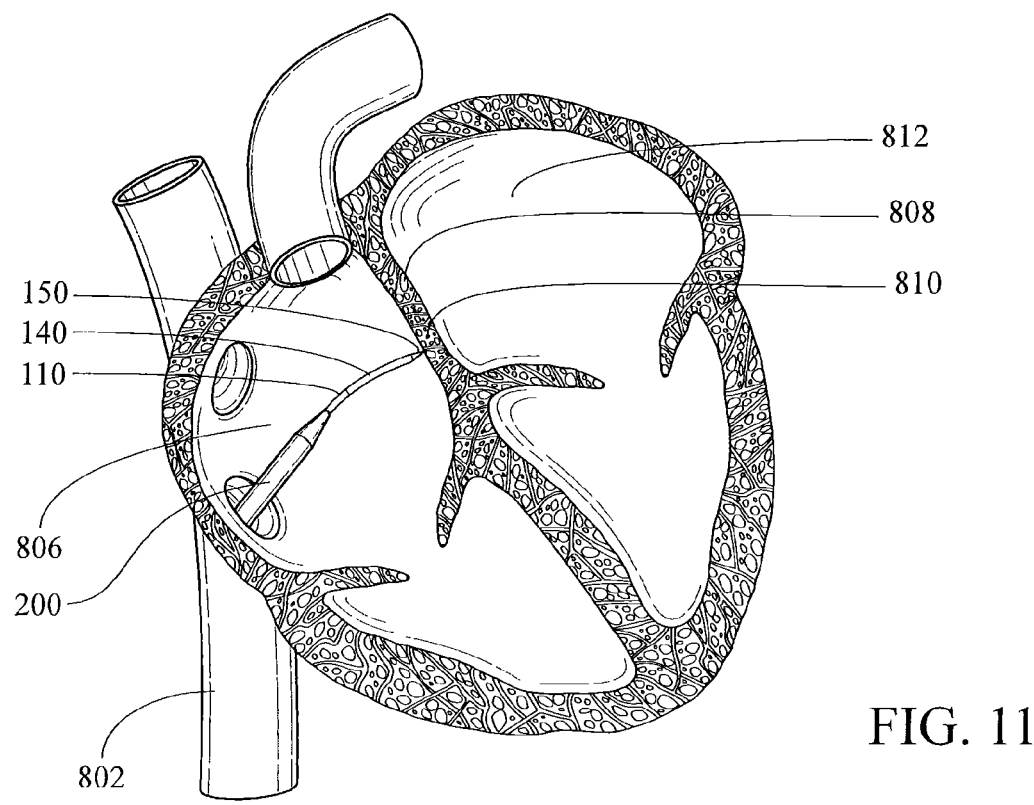
FIG. 11 illustrates a distal portion of a catheter and a distal portion of a needle in a deflected configuration positioned within a right atrium of the heart of FIG. 8.

The orientation of the needle tip 150 with respect to the first segment 130 of the cannula 110 may be adjusted as described above to align the needle tip 150 with the desired puncture point. To that end, the second segment 140 of the cannula 110 may be deflected relative to the first segment 130 of the cannula as shown in FIG. 11. The second segment 140 may be deflected to any allowable degree (i.e., to any angle of deflection) relative to the first segment 130 to position the needle tip 150 as desired within the right atrium 806. For example, the second segment 140 of the cannula 110 may be deflected relative to the first segment 130 to a sufficient degree to align the needle tip 150 with the fossa ovalis 810. The needle 100 and/or the catheter 200 also may be rotated about the longitudinal axes of the needle and the catheter to aid in properly aligning the needle tip 150 as desired.

Figure 12:
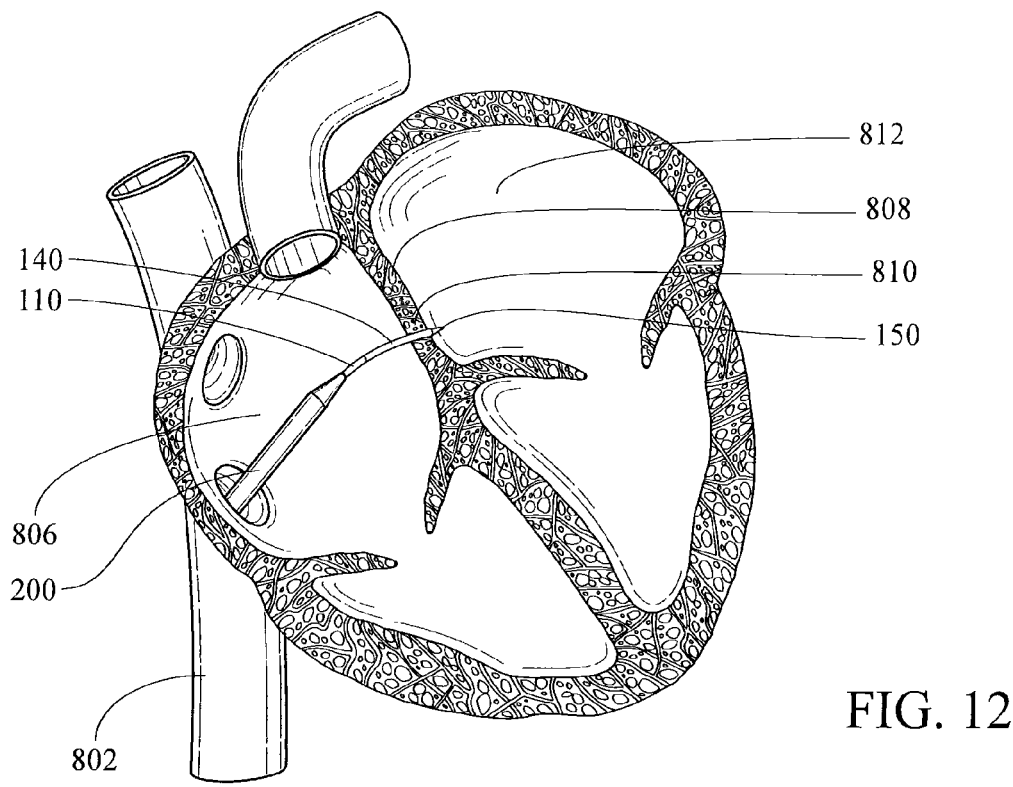
FIG. 12 illustrates a distal end of a needle penetrating an interatrial septum of the heart of FIG. 8.

After aligning the needle tip 150 with the desired puncture point along the interatrial septum 808, the needle 100 and the catheter 200 may be further advanced distally. Upon such advancement, the needle tip 150 of the cannula 110 may puncture the interatrial septum 808 as shown in FIG. 12. The pressure at the distal end 154 of the needle tip 150 may be measured as described above. The physician may use this pressure measurement to confirm the position of the distal end 154 of the needle tip 150. For example, if the measured pressure corresponds to a known or expected left atrial pressure, the position of the needle tip 150 within the left atrium 812 may be confirmed. In another example, a contrast fluid may be introduced through the lumen 118 of the cannula 110 and out through the end opening 158 of the needle tip 150. The contrast fluid may be visualized using any suitable visualization technique including, for example, x-ray, magnetic resonance imaging, or ultrasound, to confirm the location of the distal end 154 of the needle tip 150.

Figure 13:
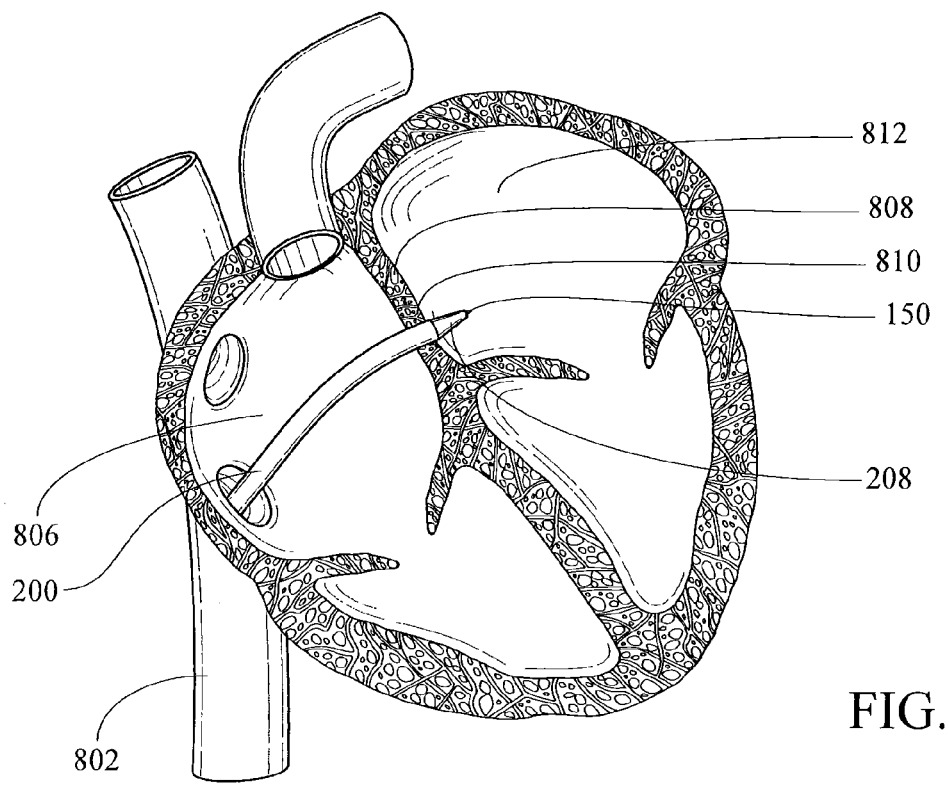
FIG. 13 illustrates a distal portion of a catheter and a distal portion of a needle positioned within a left atrium of the heart of FIG. 8.

After confirming the position of the distal end 154 of the needle tip 150 within the left atrium 812, the needle 100 and the catheter 200 may be further advanced distally until the tapered distal end 208 of the catheter passes through the interatrial septum 808 as shown in FIG. 13. The taper of the distal end 208 may enable the catheter 200 to pass smoothly through the puncture in the interatrial septum 808 formed by the needle tip 150. The tapered distal end 208 of the catheter 200 may minimize damage to the interatrial septum 808 upon passing the catheter therethrough. The position of the distal end 208 of the catheter 200 within the left atrium 812 may be confirmed using any suitable visualization technique as described above. The needle 100 may be retracted proximally relative to the catheter 200 until the needle tip 150 exits the proximal end 203 of the catheter. Additional medical devices and/or therapeutic agents may be introduced into the left atrium 812 through the catheter 200 after removal of the needle 100 therefrom.

The ability to deflect the second segment 140 of the cannula 110 relative to the first segment 130 of the cannula may enable precise adjustment of the position of the needle tip 150 during the procedure described above. Such adjustment of the position of the needle tip 150 may be beneficial to precisely puncture the interatrial septum 808 at a desired location. The ability to adjust the position of the needle tip 150 after the needle tip has been positioned within the right atrium, without removing and then reintroducing the needle 100 within the catheter 200, may reduce the time and/or complexity of a transseptal puncture procedure. The deflectable second segment 140 may be advantageous as compared to curved needles. For example, a curved needle may have an angle of curvature that is not suitable for a specific anatomy. Additionally, a curved needle may lose its curvature (i.e., it may be at least partially straightened) as the needle is navigated to a desired location within the patient's body. The deflectable second segment 140 of the cannula 110 also may be advantageous as compared to a needle delivered within a deflectable sheath. For example, the handle of the needle 100 may be less bulky and/or easier to operate than the handle of a deflectable sheath as described above.

It is intended that the foregoing detailed description of medical devices and methods be regarded as illustrative rather than limiting, and that it be understood that it is the following claims, including all equivalents, that are intended to define the spirit and scope of this invention. Terms are to be given their reasonable plain and ordinary meaning. Also, the embodiment of any figure and features thereof may be combined with the embodiments depicted in other figures. Other features known in the art and not inconsistent with the structure and function of the present invention may be added to the embodiments.

Drawings in the figures illustrating various embodiments are not necessarily to scale. Some drawings may have certain details magnified for emphasis, and any different numbers or proportions of parts should not be read as limiting, unless so-designated in the present disclosure. Those skilled in the art will appreciate that embodiments not expressly illustrated herein may be practiced within the scope of the present invention, including those features described herein for different embodiments, and may be combined with each other and/or with currently-known or future-developed technologies while remaining within the scope of the claims presented here. Moreover, the advantages described herein are not necessarily the only advantages of the invention and it is not necessarily expected that every embodiment of the invention will achieve all of the advantages described. It is therefore intended that the foregoing detailed description be regarded as illustrative rather than limiting. And, it should be understood that the following claims, including all equivalents, are intended to define the spirit and scope of this invention.

We claim:

1. A method of puncturing an interatrial septum between a right atrium and a left atrium of a heart, the method comprising:
    introducing a distal end of a catheter endoluminally into the right atrium, the catheter comprising a first elongate tubular member;
    introducing a distal end of a cannula into the right atrium, the cannula comprising a second elongate tubular member having a proximal first segment and a distal second segment, a first wire being attached to the distal second segment and configured to resist longitudinal compression of the distal second segment, and a second wire being attached near a distal end of the cannula and extending to a mechanism at a proximal end of the cannula, the distal second segment comprising a longitudinally compressible circumferential portion and being deflectable away from a linear configuration relative to the proximal first segment, a needle tip being provided at a distal end of the distal second segment of the cannula, the needle tip having a lumen in fluid communication with a lumen of the cannula and a distal end having a distal end opening, at least a portion of the cannula being disposed within a lumen of the catheter; and
    deflecting the distal second segment of the cannula in the right atrium to a deflected configuration by actuating the second wire to exert a longitudinal force on the longitudinally compressible circumferential portion and the first wire resisting longitudinal compression along another circumferential portion of the distal second segment, the needle tip thereby being aligned with a target point on the interatrial septum.

2. The method of claim 1, further comprising penetrating the target point on the interatrial septum with the needle tip to form a penetration through the interatrial septum and positioning the distal end of the needle tip in the left atrium.

3. The method of claim 2, further comprising measuring a pressure at the distal end of the needle tip to confirm the position of the distal end of the needle tip in the left atrium.

4. The method of claim 2, further comprising introducing a contrast fluid into the lumen of the cannula to deliver the contrast fluid through the distal end opening of the needle tip to confirm the position of the distal end of the needle tip in the left atrium.

5. The method of claim 2, further comprising passing the distal end of the catheter through the penetration formed through the interatrial septum and positioning the distal end of the catheter in the left atrium.

6. The method of claim 1, wherein the distal end of the catheter is tapered.

7. The method of claim 1, wherein an outer wall of the second segment of the cannula comprises a coil having a series of windings, each winding of the coil spaced from an adjacent winding of the coil.

8. The method of claim 1, wherein an outer wall of the first segment of the cannula is substantially solid.

9. The method of claim 1, wherein an outer wall of the first segment of the cannula comprises a coil having a series of windings, each winding of the coil in contact with an adjacent winding of the coil.

10. The method of claim 1, wherein the cannula comprises an inner liner, the inner liner comprising a tubular member positioned within the lumen of the cannula and extending longitudinally along at least a portion of a length of the cannula.

11. The method of claim 1, wherein the cannula comprises an outer layer positioned circumferentially around the cannula and extending longitudinally along at least a portion of a length of the cannula.

12. The method of claim 1, wherein wherein the second wire extends generally longitudinally within the lumen of the cannula.

13. The method of claim 12, wherein the mechanism at the proximal end of the cannula comprises a handle and retracting the second wire proximally relative to the cannula comprises retracting a movable portion of the handle proximally relative to a fixed portion of the handle.

14. The method of claim 13, wherein the handle is configured for one-handed operation.

15. The method of claim 1, wherein, during the step of introducing the distal end of the cannula into the right atrium, the distal end of the needle tip is positioned within the lumen of the catheter.

16. The method of claim 15, further comprising retracting the catheter proximally to expose the distal end of the needle tip in the right atrium.

17. The method of claim 1, further comprising retracting the cannula proximally relative to the catheter to remove the cannula from the lumen of the catheter, the distal end of the catheter being positioned within the left atrium.

18. The method of claim 1, wherein an outer wall of the second segment of the cannula comprises a coil having a series of windings, each winding of the coil spaced from an adjacent winding of the coil, and the first and second wires extend generally longitudinally within the lumen of the cannula.

19. The method of claim 18, further comprising penetrating the target point on the interatrial septum with the needle tip to form a penetration through the interatrial septum and positioning the distal end of the needle tip in the left atrium, measuring a pressure at the distal end of the needle tip to confirm the position of the distal end of the needle tip in the left atrium, passing the distal end of the catheter through the penetration formed through the interatrial septum and positioning the distal end of the catheter in the left atrium, and wherein the distal end of the catheter is tapered.

* * * * *